US00PP36580P3

(12) United States Plant Patent
Kolster et al.

(10) Patent No.: US PP36,580 P3
(45) Date of Patent: Apr. 1, 2025

(54) ***HYDRANGEA* PLANT NAMED 'Hokomagrefip'**

(50) Latin Name: *Hydrangea macrophylla*
Varietal Denomination: Hokomagrefip

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 18/811,719

(22) Filed: Aug. 21, 2024

(65) Prior Publication Data

US 2025/0072304 P1 Feb. 27, 2025

(30) Foreign Application Priority Data

Aug. 23, 2023 (QZ) ..... PBR 20231747

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Penny J. Aguirre

(57) ABSTRACT

A new cultivar of *Hydrangea macrophylla* plant named 'Hokomagrefip' that is characterized by its mophead inflorescences with sterile sepals that are pink-red in color with markings of green, its sturdy sterile sepals, its abundant strong stems, and its dark green foliage.

4 Drawing Sheets

Botanical classification: *Hydrangea macrophylla.*
Varietal denomination: 'Hokomagrefip'.

CROSS-REFERENCE TO RELATED APPLICATION

This application claims priority to European Community Plant Variety Office (C.P.V.O.) Plant Breeder's Rights Application No. 2023/1747 filed on Aug. 23, 2023, under 35 U.S.C. 119(f), the entire contents of which is incorporated by reference herein. The information for the plant breeders' rights application was received directly from the Inventors.

BACKGROUND OF THE INVENTION

The present invention relates to a new and distinct cultivar of *Hydrangea macrophylla* and will be referred to hereafter by its cultivar name, 'Hokomagrefip'. 'Hokomagrefip' represents a new bigleaf *Hydrangea*, a perennial shrub grown for landscape use and as a potted plant.

'Hokomagrefip' derived from an ongoing controlled breeding program directed by the Inventor. A goal of the breeding program included developing a new cultivar of *Hydrangea* that is suitable for container growing with bi-colored and sturdy sterile sepals.

'Hokomagrefip' arose from a controlled cross made by the Inventor in Boskoop, The Netherlands in June of 2015 between unnamed and unpatented proprietary plants in the Inventor's breeding program; reference no. 11-026-002 as the female parent and reference no. 14-023-016 as the male parent. 'Hokomagrefip' was selected as a single unique plant from amongst the resulting seedlings in May of 2017.

Asexual propagation of the new cultivar was first accomplished by stem cuttings by the Inventor in Boskoop, The Netherlands in August of 2017. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomagrefip' as a unique cultivar of *Hydrangea macrophylla.*

1. 'Hokomagrefip' exhibits mophead inflorescences with sterile sepals that are pink-red in color with markings of green.
2. 'Hokomagrefip' exhibits sturdy sterile sepals.
3. 'Hokomagrefip' exhibits abundant strong stems.
4. 'Hokomagrefip' exhibits dark green foliage.

The female parent of 'Hokomagrefip' differs from 'Hokomagrefip' in having smaller inflorescences with sterile sepals that are light pink in color, leaves that are lighter green in color, and weaker branches. The male parent of 'Hokomagrefip' differs from 'Hokomagrefip' in having inflorescences with sterile sepals that are much darker red and green in color and foliage that is darker green in color. 'Hokomagrefip' can be most closely compared to the *Hydrangea macrophylla* cultivars 'Hokomathyst' (U.S. Pat. No. 22,261) and 'Qufu' (U.S. Pat. No. 26,426). Both are similar to 'Hokomagrefip' in having sterile sepals flowers that are bi-colored and foliage that is dark in color. 'Hokomathyst' differs from 'Hokomagrefip' in having sterile flower sepals that are more pink (less red) and green in color, less branching, and a more vigorous growth habit. 'Qufu' differs from 'Hokomagrefip' in having sterile sepals that are more pink (less red) and green in color and less branching.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include a website listing by Plants Nouveau.

BRIEF DESCRIPTION OF THE DRAWINGS

The accompanying color photographs illustrate the overall appearance and distinct characteristics of the new *Hydrangea*. The photographs were taken of a two-year-old plant of 'Hokomagrefip' as grown outdoors in 20-cm containers in Vineland Station, Ontario, Canada.

The photograph in FIG. 1 provides a side view of the plant habit of 'Hokomagrefip' in bloom with mature inflorescences.

Figure 1:
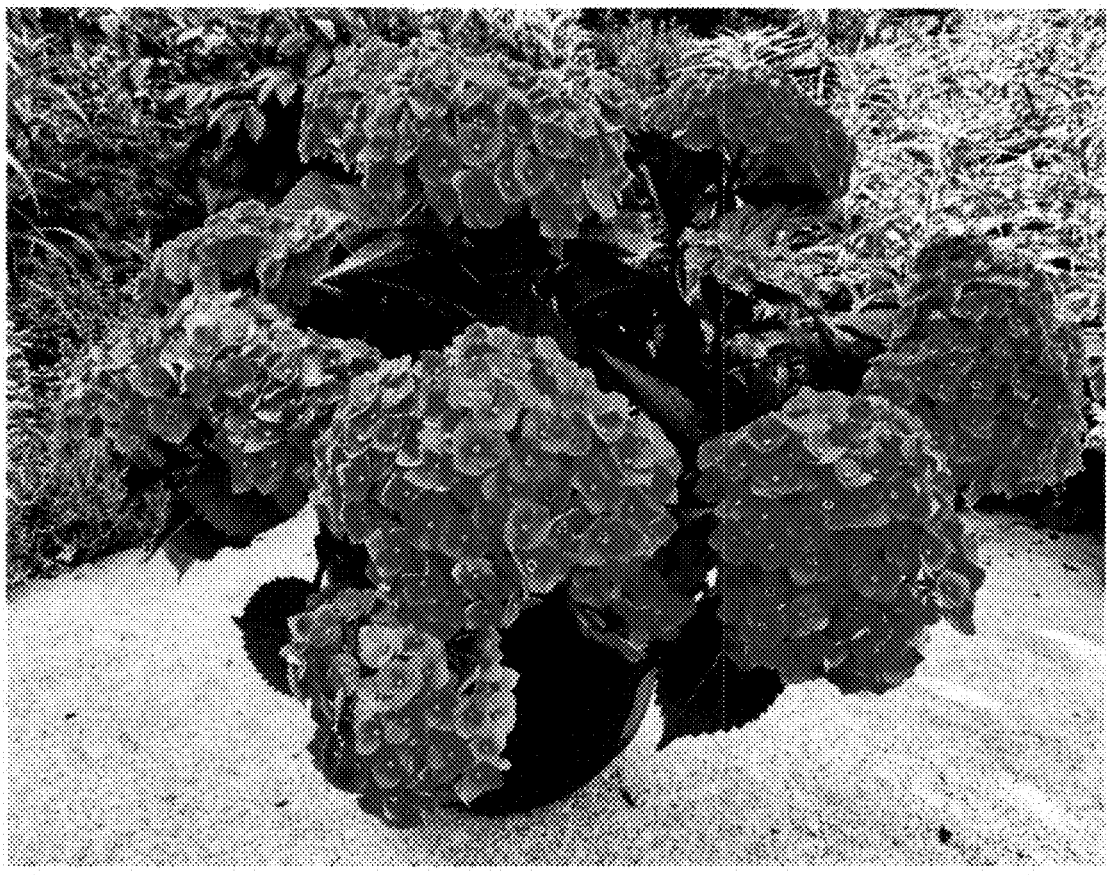
Figure 2:
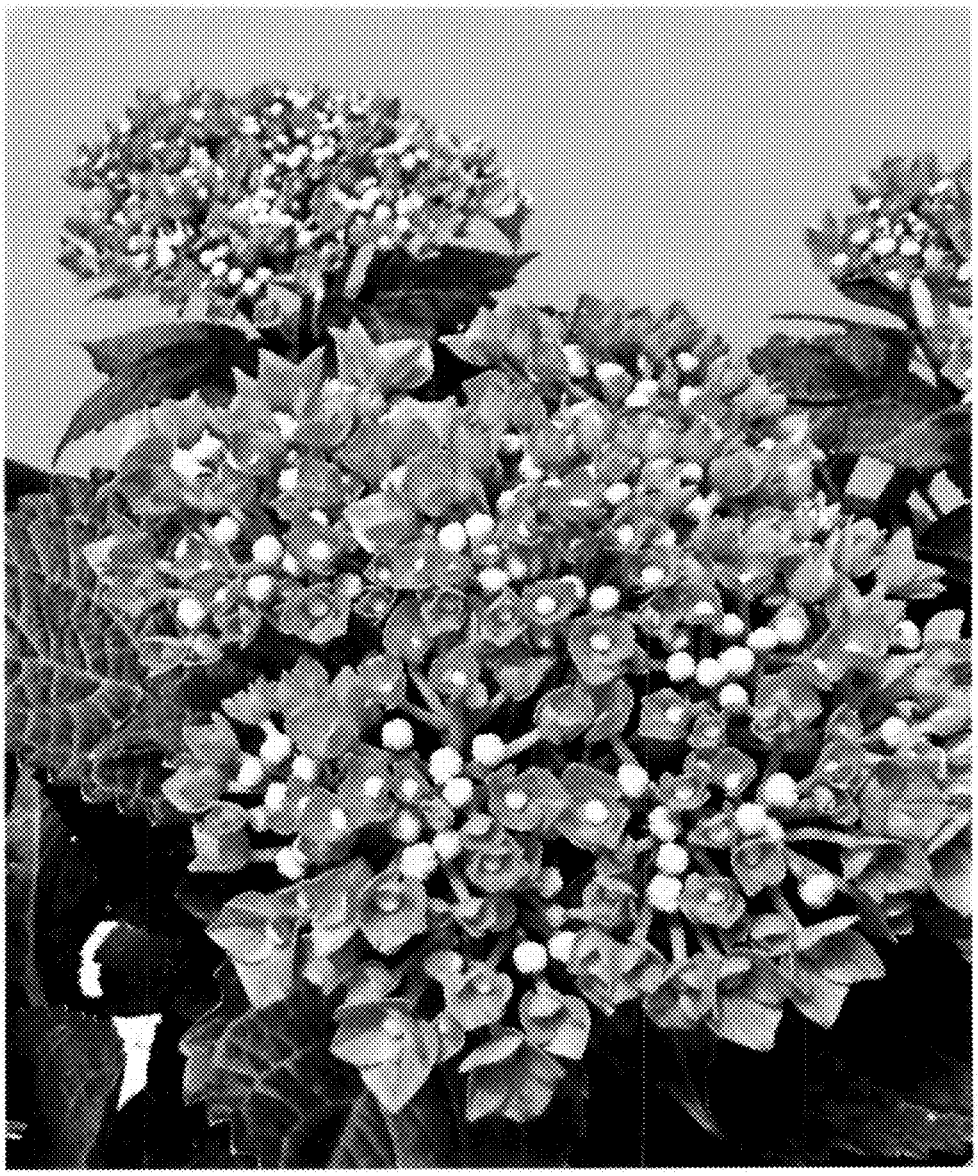

The photograph in FIG. 2 provides a close-up view of young inflorescences of 'Hokomagrefip'.

Figure 3:
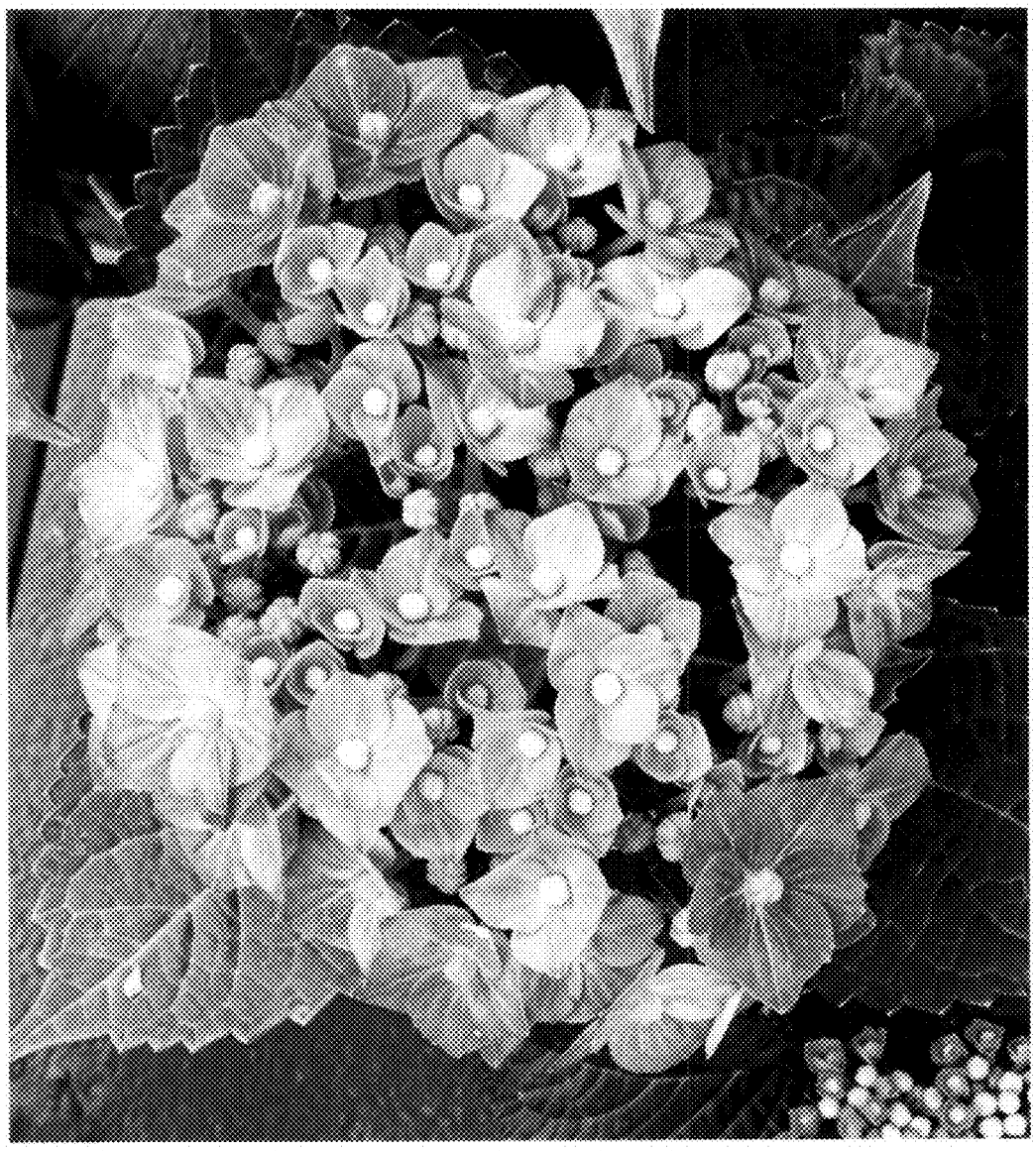

The photograph in FIG. 3 provides a close-up view of maturing inflorescences of 'Hokomagrefip'.

Figure 4:
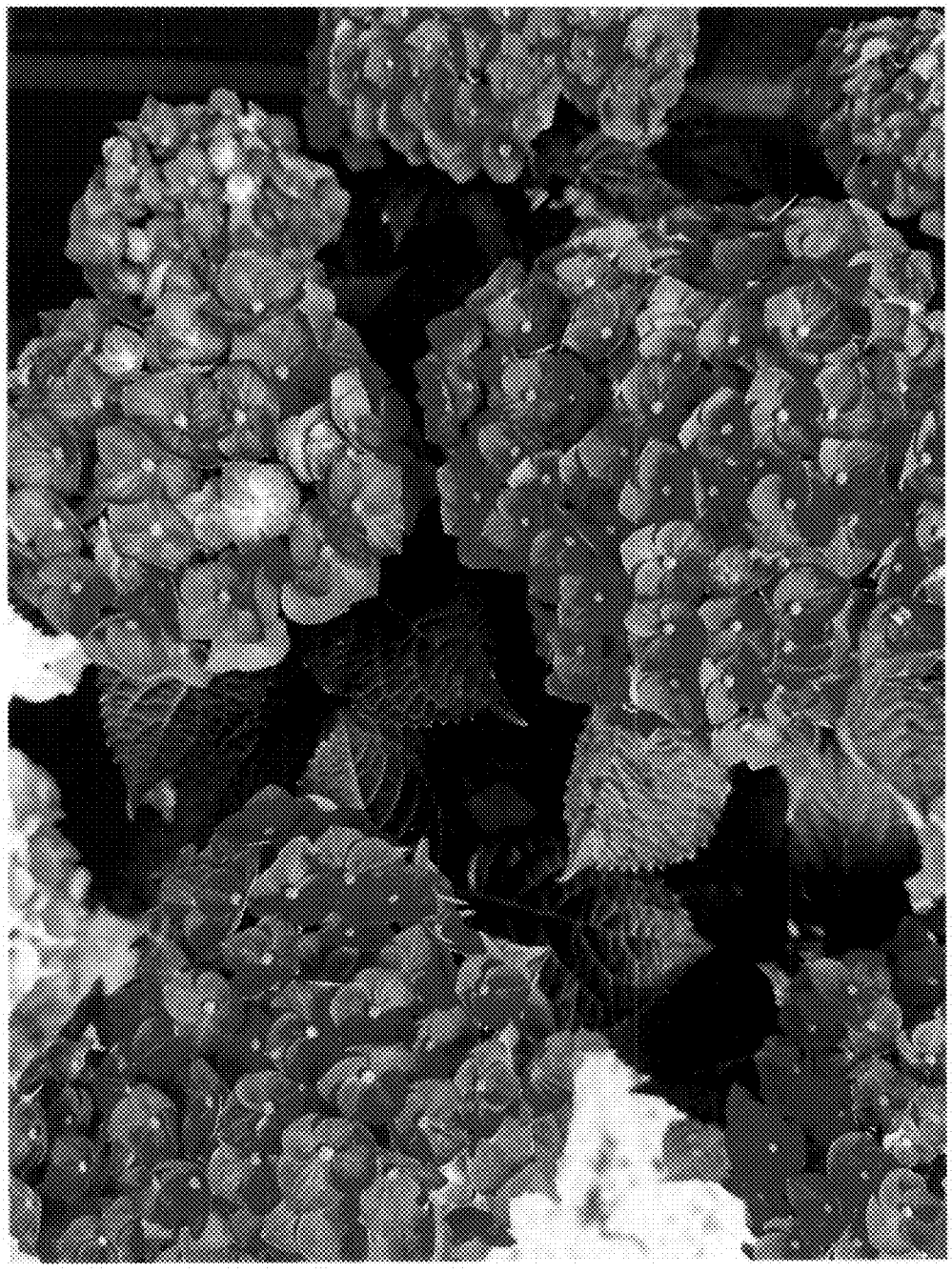

The photograph in FIG. 4 provides a close-up view of the mature inflorescences of 'Hokomagrefip'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'Hokomagrefip' as grown outdoors in 20-cm containers in Vineland Station, Ontario, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—At least 2 months in color from May to July in The Netherlands.

*Plant type.*—Deciduous shrub, mophead type *Hydrangea.*

*Plant habit.*—Upright, compact, well branched.

*Height and spread.*—An average of 37 cm in in height and 47 cm in spread as a two-year-old plant as grown in a container and 1 m in height and spread as a mature plant in the landscape.

*Hardiness.*—At least U.S.D.A. Zones 5 to 9.

*Disease and pest resistance.*—No susceptibility and resistance to diseases or pests has been observed.

*Root description.*—Fine and fibrous, 162C in color.

*Propagation.*—Stem cuttings.

*Root development.*—An average of 3 weeks for root initiation with a young rooted plant produced in an average of six weeks.

*Growth rate and vigor.*—Moderate.

Stem description:

*Stem shape.*—Oval.

*Stem strength.*—Very strong.

*Stem color.*—Young and mature; 144A, flushed at base of petiole attachment 183A, woody bark; a blend of N200A and 177B.

*Stem size.*—Main; 3 cm in length, 4 mm in diameter, lateral; 29 cm in length, 6 mm in diameter.

*Stem surface.*—Young and mature; glabrous, glossy, sparsely covered with lenticels 10 per 1 cm area, 0.5 mm in length, 0.3 mm in width, 187A in color, woody bark; glabrous in areas and exfoliating in areas, matte.

*Stem aspect.*—Upright to slightly outward.

*Internode length.*—An average of 4 cm.

*Branching.*—Freely branching, average of 3 main branches, 10 lateral branches per main branch.

Foliage description:

*Leaf shape.*—Ovate.

*Leaf arrangement.*—Opposite.

*Leaf division.*—Simple.

*Leaf base.*—Cuneate.

*Leaf apex.*—Apiculate.

*Leaf margins.*—Bluntly serrate.

*Leaf venation.*—Pinnate, upper surface; 145A, lower surface; 145A to 145B.

*Leaf size.*—An average of 8 cm in length and 6 cm in width.

*Leaf attachment.*—Petiolate.

*Leaf number.*—An average of 10 per lateral stem.

*Leaf surface.*—Both surfaces; glabrous, slightly glossy with a slight sheen.

*Leaf color.*—Young foliage; upper surface a blend of 144A and 144B, lower surface 145B, mature foliage; upper surface 147A, lower surface 147C.

*Petioles.*—Flattened and concave, strong, average of 2 cm in length, 3 mm in diameter, upper surface 144D in color, lower surface 144C in color, both surfaces glossy with a reflective sheen, glabrous.

Inflorescence description:

*Inflorescence type.*—Terminal panicle, rounded mophead in form comprised of sterile flowers and fertile flowers.

*Lastingness of inflorescence.*—Sterile flowers; persistent for an average of 5 weeks, fertile flowers; an average of 5 days, self-cleaning.

*Inflorescence number.*—One per lateral stem.

*Inflorescence size.*—An average of 6 cm in height and 12 cm in diameter.

*Flower number.*—An average of 150 sterile flowers and 75 fertile flowers per panicle.

*Flower fragrance.*—None.

*Flower aspect.*—Upright to outward.

*Flower size.*—Sterile flowers; an average of 1.5 cm in diameter, 1 cm in depth, fertile flowers; an average of 3 mm in diameter, 2 mm in depth.

*Flower type.*—Rotate.

*Flower buds.*—Sterile flowers; an average of 3 mm in length and 2 mm in diameter, oval in shape, 144A in color, fertile flowers; 2.7 mm in length, 3 mm in diameter, broad obovate in shape, young; 145B to 145C in color, occasionally lightly flushed with 186A to 186B, mature; NN155D, flushed with 77B, 77C, and 73D.

*Peduncles*.—Primary peduncle; very strong, flattened oval in shape, an average of 2 cm in length and 2 mm in diameter, a blend of 144A to 144B in color, surface is glossy, moderately covered with pubescence, soft hairs; minute in size, 157C in color, also sparsely covered with lenticels; average of 5 per 1 cm area, 185A in color, an average of 1 mm in length, 0.5 mm in width, secondary peduncles; moderately strong and flexible, rounded in shape, an average of 1 cm in length and 2 mm in diameter, a blend of 144A to 144B in color, surface is glossy, densely covered with pubescence, soft hairs minute in size, 157C in color, also sparsely covered with lenticels; average of 2 per 1 cm area, 187A in color, an average of 0.8 mm in length and width.

*Pedicels*.—Sterile and fertile flowers; held in multiple angles from the secondary peduncle, moderately strong and flexible, rounded in shape, an average of 0.8 cm in length and 1 mm in diameter, a blend of 144B in color, surface is glossy, densely covered with pubescence, soft hairs minute in size, matches surface color.

*Petals*.—Sterile flowers: petal spot; 2 mm in depth and 1 mm in diameter, round in shape, color; 157B, petals; an average of 4, rotate in arrangement, acute-rounded apex, cuneate base, entire margins, elliptic and concave in shape, an average of 3 mm in length and 2 mm in width, both surfaces; glabrous and dull, color; upper and lower surface when opening; 157B, when fully open upper and lower surface; NN155D, flushed with 77B, 77C, and 73D, fertile flowers: petal spot; 2 mm in depth and 1 mm in diameter, round in shape, color; 157B, petals; an average of 5, rotate in arrangement, elliptic and slightly concave in shape, entire margins, acute apex, cuneate base, an average of 4 mm in length and 2 mm in width, upper and lower surface glabrous and dull, color: upper and lower surface when opening; 145A and 144A, upper and lower surface when fully open; NN155C, flushed with 68B.

*Sepals*.—Sterile flowers; ranging between 3 to 5, rotate arrangement, overlapping, bluntly acute apex, deltoid to broadly ovate in shape, entire margins, very slightly wavy and concave in aspect, up to 1.5 cm in length and 1.7 cm in width, both surfaces; glabrous and dull, color; upper and lower surfaces when opening; (spring) 144A, upper and lower surface when fully open; 144B, occasionally flushed with 181A at the apex, upper and lower surface maturing; (late spring) becomes flushed and mottled with a blend of N74A and 149A, and turns fully to N74A and 185A with some outer tips becoming 60A, (summer) becomes mostly 63A to 63B, center lightly flushed with 67A, margins and tip occasionally mottled N148B (fall) sepals mature non-fading until browning, fertile flowers; minute, stay fused around base of petals, an average of 5, acuminate in shape, entire margin, lanceolate apex, 0.3 mm in length and width, and truncate base, surfaces are glossy, color; 143A.

Reproductive organs:

*Stamens*.—Sterile flowers; an average of 9, anthers; bifid, broad shaped, an average of 1 mm in width, 0.8 mm in depth, 203A in color, filaments; an average of 2 mm in length, 61B in color, pollen; moderate to high, 155A in color, fertile flowers; an average of 10, anthers club-shaped, an average of 1 mm in diameter, 203A in color, filaments; an average of 2 mm in length, N74A in color, pollen; moderate to high, 155A in color.

*Pistils*.—Sterile flowers; 1, 3-lobed, 2 mm in length and width, stigmas; club-shaped and 155A in color, styles; an average of 1 mm in length and 155A in color, ovary; superior, 144B in color, triangular in shape, 3 mm in length and width, fertile flowers; 1, 3-lobed, 3 mm in length, 2 mm in width, stigmas; club-shaped, 68B in color, styles; an average of 1.5 mm in length and 68A in color, ovary 68A in color, triangular in shape, 1 mm in diameter.

*Fruit and seed*.—None observed to date.

It is claimed:

1. A new and distinct cultivar of *Hydrangea* plant named 'Hokomagrefip' substantially as herein illustrated and described.

* * * * *